United States Patent [19]
Golz et al.

[11] Patent Number: 5,916,577
[45] Date of Patent: Jun. 29, 1999

[54] COSMETIC WITH CONDENSATES OF PLANT AND ANIMAL DECOMPOSITION PRODUCTS

[75] Inventors: Karin Golz; Leonhard Zastrow, both of Monaco, Monaco; Klaus Stanzl, White Plains, N.Y.; Ulrich Klügel, Berlin, Germany; Günter Westphal, Berlin, Germany; Leander Schöbel, Berlin, Germany

[73] Assignee: Lancaster Group GmbH, Ludwigshafen, Germany

[21] Appl. No.: 08/875,798

[22] PCT Filed: Mar. 22, 1996

[86] PCT No.: PCT/DE96/00548

§ 371 Date: Jul. 17, 1997

§ 102(e) Date: Jul. 17, 1997

[87] PCT Pub. No.: WO96/29048

PCT Pub. Date: Sep. 26, 1996

[51] Int. Cl.⁶ .......................... A61K 35/78; A61K 35/20; A61K 7/06; A61K 7/48
[52] U.S. Cl. .......................... 424/401; 424/535; 424/520; 424/195.1; 510/119; 510/130
[58] Field of Search ................ 424/195.1, 535, 424/520, 401; 510/119, 129, 130

[56] References Cited

U.S. PATENT DOCUMENTS

| | | | |
|---|---|---|---|
| 4,716,120 | 12/1987 | Tsay et al. | 436/513 |
| 4,853,430 | 8/1989 | Stühler et al. | 524/604 |
| 5,071,960 | 12/1991 | Turowsi et al. | 530/356 |
| 5,422,111 | 6/1995 | Huc et al. | 424/401 |

FOREIGN PATENT DOCUMENTS

| | | | |
|---|---|---|---|
| 0417619 | 3/1991 | European Pat. Off. | C11D 1/32 |
| 273 276 | 11/1989 | Germany | C11D 1/32 |
| 4403774 | 8/1995 | Germany | A61K 7/48 |
| 07033621 | 2/1995 | Japan | A61K 7/00 |
| WO 97/14713 | 4/1997 | WIPO | C07K 14/415 |

OTHER PUBLICATIONS

Foss, N.E. in American Pharmacy. R.A. Lyman, J.B. Sprowis, G. Urdand, eds. J.B. Lippincott Co., Philadelphia (1955), p. 157. No month found.

Roberts, et al. In Cellulosics: Chemical, Biochemical and Material Aspects, J.F. Kennedy, G.O. Phillips, P.A. Williams, eds. Ellis Horwood Ltd., Great Britain (1993), pp. 141–151. No month found.

International Cosmetic Ingredient Dictionary. J.A. Wenninger, G.N. McEwen, eds. CTFA, Washington D.C. (1993). No month found.

Majors, R. LC–GC 14(2), pp. 89–96. (Feb. 1996).

Lehniger, A.L. Biochemistry, second ed. Worth Publishers, New York. (1975), pp. 141–153. No month found.

*Primary Examiner*—Kathleen K. Fonda
*Assistant Examiner*—Marjorie A. Moran
*Attorney, Agent, or Firm*—Collard & Roe, P.C.

[57] ABSTRACT

The invention concerns cosmetic agents with condensates of plant and animal decomposition products, which can be used in cosmetic body care and cleansing preparations and which, in addition to the emulsifying effect, have essential skin-care properties. The object of the invention is to prepare cosmetic products from plant and animal starting materials, said products having substantial portions of original biological structures but being modified to such an extent that they are cosmetically acceptable owing to their neutral smell and pale color. According to the invention, the cosmetic agent is a product of a direct and mild (20 to 55° C.; pH 7.5 to 8.5) decomposition of a biological starting material in an aqueous medium, subsequent condensation with a substoechiometric amount of a $C_{10}$ to $C_{20}$ fatty acid halide or mixture and optionally subsequent etherification or esterification of the condensation product. The starting materials can be yeasts, yeast fractions, pulses, pulse fractions, pectins, pectin-containing masses, algae, algae fractions, animal milk, animal milk fractions and their mixtures, and contain helical natural substance components, enzyme structures and vitamin structures.

26 Claims, No Drawings

COSMETIC WITH CONDENSATES OF PLANT AND ANIMAL DECOMPOSITION PRODUCTS

This case claims priority under 35 U.S.C. 120 to PCT/De96/00548, filed Mar. 22, 1996.

The invention concerns cosmetic agents with condensates of plant and animal decomposition products, which can be used in cosmetic body care and cleansing preparations and which, in addition to the emulsifying effect, have essential skin-care properties.

Cosmetic agents with emulsifying and surface-active effects are known in many combinations for use in cosmetic products for body care and cleansing. Among them there are two classes of tensides in particular which are particularly characterized by good skin tolerance and are accessible from natural raw materials, and which are becoming of growing interest, namely the protein-fatty acid condensates and the alkyl polyglycosides. The protein-fatty acid condensates are obtained by the transformation of protein partial hydrolysates with fatty acids, fatty acid chlorides, or fatty acid anhydrides in an aqueous solution, with the addition of bases. As fatty acid components, use may be made of derivatives of plant fatty acids (coconut oil fatty acids, oleic acid, and others), or those from synthetic fatty acids with identical chain lengths.

The corresponding protein hydrolysates are derived from alkaline, acidic, or enzymatic hydrolysis of natural proteins or raw materials containing proteins. Starting materials are plant, animal, microbial, and synthetic proteins, such as casein, albumin, osteocolla, gelatines, keratin, scrap leather, collagen, silk peptides, and biomasses on a paraffin base. For the alkaline decomposition of substances containing protein, alkali or alkaline earth compounds are used, as are their hydroxides, or ammonia, at increased temperature and, if applicable, at increased pressure.

The advantageous properties of the alkyl polyglycosides and the protein-fatty acid condensation products for cosmetic applications consist, in terms of their accessibility, of natural raw materials, of which the freedom from ethylene oxide, the viscosity of mixtures, the good foaming properties, the hair-conditioning properties, the synergistic effect with other tensides, and, last but not least, their biodegradability and good dermatological tolerance. With these products, however, the original biological structures are essentially no longer retained.

The object of the invention is to provide cosmetic agents and cosmetics with very good tolerance for the skin and mucous membranes, as well as skin-care properties, from plant and animal starting materials, which essentially contain proportions of original biological structures, but have been modified to the extent that they are cosmetically acceptable thanks to their neutral smell and light colour.

According to the invention, this objective is achieved by a cosmetic which contains an unpurified, cosmetically-effective product of a direct and mild decomposition (20 to 55° C.; pH 7.5–8.5) of a biological starting material, selected from the group which consists of yeasts, yeast fractions, pulses, pulse fractions, pectins, pectin-containing masses, algae, algae fractions, animal milk, animal milk fractions, and their mixtures, in an aqueous medium, and condensed with a sub-stoichiometric amount of a $C_{10}$–$C_{20}$ fatty acid halide or a $C_{10}$–$C_{20}$ fatty acid halide mixtures, in which context the condensed decomposition product contains biological structures of the starting material, selected from the group which consists of helical natural substance components, vitamin structures, and their mixtures.

If the biological starting material is a yeast or yeast fraction, this is selected from the group which consists of baker's yeast and brewer's yeast. Brewer's waste yeast with a solid substance content of 10 to 30 percent by weight or yeast biomass fractions with yeast cell residues, such as are obtained after protein extraction in the yeast processing industry as a byproduct, can also be used.

If the biological starting material is a pulse or a pulse fraction, this is selected from the group which consists of peas, lentils, soya beans, and broad beans.

If the biological starting material is a pectin or a mass containing pectin, these are, in particular, citrus peels and pomace, as well as grape daff.

If the biological starting material is an algae or an algae fraction, this is selected from the group which consists of green algae, brown algae, and red algae, in which context these algae contain high proportions of chlorophyll, alginates, proteins, and mineral substances.

If the biological starting material is animal milk or an animal milk fraction, this is selected from the group consisting of mare's milk, cow's milk, sheep milk, reindeer milk, and goat's milk.

A particularly preferred starting material is mare's milk.

Biological starting materials of which the constituents are not directly accessible by chemical reaction, because they are present in their biological cell structure, are homogenised and broken down by the effect of ultrasonics and/or mechanical shearing forces. This has the advantage, in comparison with the alkaline decomposition of cell structures of the state of the art, that enzyme and vitamin activities are, to a large extent, retained. The ultrasonic treatment is effected at temperatures of not above 55° C. and at pH values of between 6 and 8. Ultrasonic treatment is particularly well-suited with biological starting materials such a yeasts and pulses.

The biological starting material, which has been pretreated as appropriate by ultrasonics or mechanical shearing forces, is adjusted to a solid substance content of 15 to 30 percent by weight and a pH value of 7.5 to 8.5. Conversion of the suspensions then takes place with a sub-stoichiometric quantity of acid halides of plant fatty acids or synthetic fatty acids, with chain lengths from 10 to 20 carbon atoms, and for preference 12 to 18 carbon atoms, at temperatures from 20 to 55° C. (condensation). It is also possible to use fatty acids with different chain lengths from the range indicated above.

The adjustment of the pH value in the alkaline range is effected for preference with alkaline metal hydroxide solutions or alkali carbonates. The addition of appropriate alkaline earth compounds is likewise possible, but this has the disadvantage that the corresponding salts remain as insoluble constituents in the end product.

Of the fatty acid halides, the chlorides are particularly preferred. As fatty acids, those with 12 to 18 carbon atoms are preferred. One particularly preferred fatty acid is palmitic acid. After the conversion of the biological starting material with the fatty acid halide or fatty acid halide mixture, the products obtained in this manner can be modified to improve their properties or to adapt them for specific purposes, such as increasing the gelling capability, by introducing suitable substitutes with the aid of esterification or etherification. Carboxymethylisations with monochloroacetic acid or dicholoroacetic acid or succinylisation with succinic acid anhydride are especially preferred.

The biologically degradable and condensed products according to the invention are in the first instance of significance in cosmetics due to their extensive content of biological structures, such as helices, enzyme and vitamin structures, and they accordingly differ substantially from conventional products. The products also feature nonderivated constituents of the biological starting material or their cleavage products, such as peptides, amino acids, carbohydrates and fats, since they are used in sub-stoichiometric quantities as reaction partners for the fatty acid halides. These cleavage products of the biological starting materials possess advantageous effects on the human skin.

The term helical natural substance components in connection with the present invention is understood to mean proteins and polysaccharides which form individual helix ranges or double helix structures.

In addition to this, the biological starting materials have an emulsifying effect, and can be used as essentially non-ionic tensides with anionic fractions with this ancillary effect in creams, washing lotions, hair washing products, hair conditioners, masks or gels. In addition, they can be used as active substance stabilizers or as viscosity-enhancing components in creams or lotions, and overall feature excellent tolerance to the skin and mucous membranes, as well as beneficial properties.

Due to the differences between the constituents in the biological starting materials with regard to their chemical composition and their molecular sizes, there comes into being, during the mild decomposition according to the invention, with subsequent condensation, a mixture of different chemical compounds with a broad molecular weight distribution. As a result, instabilities in chemical preparations can to a very large extent be avoided, even in the event of varying volumetric relationships. of particular advantage is the fact that the aqueous solutions of the condensed decomposition products according to the invention, from biological starting materials of low surface tension values have tensides such as are manufactured on the basis of regrown raw materials such as protein-fatty acid condensates or alkyl polyglycosides.

The invention also concerns a process for the manufacture of cosmetically effective condensed decomposition products of vegetable and animal origin, characterized in that a biological starting material is decomposed, selected from the group consisting of yeasts, yeast fractions, pulses, pulse fractions, pectins, pectin-containing masses, algae, algae fractions, animal milk and animal milk fractions, and their mixtures, in the aqueous and weakly alkaline medium in the range from pH 7.5 to 8.5 and in the temperature range from 20 to 55° C., and condensed with a sub-stoichiometric volume of a halide of a $C_{10}$–$C_{20}$ fatty acid or of a fatty acid halide mixture of such fatty acids; the pH value is then adjusted to values in the range from 5 to 7, and the product obtained, which contains biological structures of the starting product, selected from the group consisting of the helical natural substance components, enzyme structures, and vitamin structures and their mixtures, homogenised without further splitting, and, if applicable, the homogenisate is mixed with other cosmetic substances from the group of carrier substances, ancillary substances, and active substances, and, if applicable, processed to form a cosmetic preparation, in which situation the temperature does not exceed 55° C., and the pH value of the final product is between pH 5 and 7.

To particular advantage, the adjustment of the pH value is effected in the weakly alkaline range from pH 7.5 to 8.5, with an alkali hydroxide or alkali carbonate.

To particular advantage, the adjustment of the pH value is effected in the weakly acidic range from pH 5 to 7 with an acid selected from the group consisting of hydrochloric acid, tartaric acid, malic acid, and citric acid.

To advantage, biological structures which are not directly accessible to chemical reaction are in part decomposed by the effects of ultrasonics and/or mechanical shearing forces, in which situation the temperature during decomposition does not exceed 55° C. and the pH lies in the range from 5 to 8.

One particularly advantageous decomposition product derives from an ultrasonic decomposition process with an ultrasonic flow cell according to DE 42 41 154, in which the sonotrode projects to ½ to ⅔ of its length into the flow cell, the angle of the sonotrode in the ultrasonic wave exposure vessel being in the range from 80.5 to 88.5°, the ratio of the immersion length of the synotrode (in mm) to the ultrasonic wave exposure volume (in ml) being adjusted to a value in the range from 1:1.1 to 1:20, and the ratio of the immersion length of the synotrode (in mm) to the solid substance proportion of the medium to be exposed (in mass %) lies in the range from 1:0.02 to 1:2.2.

According to the invention, the biological decomposition product can be further esterified or etherised after conversion with fatty acid halide, in order to encompass special application purposes; for example, so as to incur an improvement in the gelling capacity, or to influence other properties. One advantageous procedure is carboxymethylisation with monochloroacetic or dichloroacetic acid, or succinylisation with succinic acid anhydride.

To adjust the pH value in the weakly acidic range, for example, the acids referred to above can be used. By contrast with hydrochloric acid, however, hydroxycarbonic acids such as tartaric acid, malic acid, and, for especial preference, citric acid, have the advantage that they exert a lightening effect on the products in the course of neutralisation. In addition to this, however, hydrogen peroxide may be added, in order to effect further improvement of colour and smell. As a result, products with a milky-white to milky-light yellow or light green or light brown colour can be produced, depending on whether the starting product is animal milk or yeast or green algae or green peas, or brown algae respectively, which have a neutral or pleasant smell.

The biological starting materials decomposed and condensed according to the invention can be used without further purification in the cosmetics sector as cosmetic raw materials with care properties, as tensides or additional tenside constituents, and as regulators for the surface tension. It does, however, already represent a cosmetic substance—with the addition of only a few conventional cosmetic ancillary substances—as a result of its high proportion of active substances.

The cosmetic raw material according to the invention differs clearly from the products previously known in the high proportions of biological structures, which can be controlled to a large extent in the end product by the adjustment of the solid substance content of the biologically degraded product. For example, this solid substance content in animal milk used lies in the range from 35 to 50% by weight, related to the total mass, in order to attain a good consistency of the end product. In the case of legumes, the solid substance content is approximately in the range from 15 to 25% by weight, in order to achieve a good consistency of the end product.

The proportion of the helix structures in the decomposed biological material can be measured by means of what is referred to as the helix-coil transition analysis (Kogan et al., Biopolymers, Vol. 27, 1055–63; Williams et al., Carb. res. 219, 203–213), in which use is made of the fact that ordered structures, such as helices, form complexes with, for example, colouring agents. By contrast with a comparison substance, such as starch, absorption maxima can be measured at the corresponding NaOH concentrations. This makes it possible for specific quantities of helices to be adjusted by means of the volume of fatty acid halide used.

The term "sub-stoichiometric volume" in connection with this invention indicates that, related to the weight, 20 to 90% fatty acid halide is used in relation to 100% biological starting material. For animal milk, and mare's milk in particular, an advantageous range of the sub-stoichiometric volume, for example, is 50 to 70%.

The adjustment of a sub-stoichiometric ratio can be carried out by the determination of the functional groups of the starting material and the secondary hydroxy and amino groups. This adjustment of the ratio is therefore effected via the OH coefficient and amine coefficient (in the same way as with the manufacture of polyurethane), in that, depending on the OH or amine coefficient of a specific volume of starting material (100%) which has been determined, a lesser volume of fatty acid halide (20 to 90%) is added. Depending on what solid substance content is desired in the end product—and therefore what specific viscosities—this solid substance content can be controlled by means of the value of the shortfall of the fatty acid halide (mixture), and therefore the proportion of the biological structures.

The cosmetic substance can to advantage be presented in the form of a cream, a body lotion, a hair washing agent, a mask, or a gel.

It can, however, also be presented directly as a product of condensation or subsequent etherisation or esterisation.

The invention is explained in greater detail below on the basis of examples; the examples are not however limitative on the invention.

EXAMPLE 1

333 g of baker's yeast (30% by weight of the dry mass) was suspended with 166 ml of water, and subjected to ultrasonic treatment for one hour (appliance USD 30 from Emich Ultraschall GmbH, generator output 400 W, amplitude 50 µm). By cooling the ultrasonic exposure cell, the temperature was maintained at below 30° C. After the procedure, a yellowish-pink viscous suspension was obtained, with a pH value of 5.5. The pH value was adjusted to 8.0 with sodium hydroxide, and 60 g palmatic acid chloride was slowly added while stirring. The temperature was maintained at 50° C. and the H value at 8.0 by the addition of sodium hydroxide. After 90 minutes, 10 ml hydrogen peroxide (30%) was added, and the mixture cooled to room temperature.

The foamed mass was adjusted to a pH value of 5.5 with citric acid and homogenised.

The product had a light yellow to light grey colour, a pleasant smell identical to the raw material, and a solid substance content of 34% by weight

EXAMPLE 2

150 g of an industrial yeast protein fraction (DHW Hamburg) were dissolved in 850 ml of water, the ph value was adjusted to 8.0 and then the industrial yeast protein fraction was mixed under stirring at 55° C. with 75 g stearic acid chloride. It was stirred for 60 minutes while maintaining the temperature and pH value (addition of NaOH). 15 ml hydrogen peroxide was added during cooling, and a pH value of 6.0 was adjusted with malic acid after 15 minutes.

The product had a light brown colour and a solid substance content of 21% by weight.

EXAMPLE 3

300 g dry green shelled peas were steeped for 24 hours at room temperature in 1700 ml water, and then homogenised mechanically (Ultra-Turrax). The mass was adjusted to a pH value of 8.3 with sodium hydroxide and stirred for 60 minutes at 55° C. 144 g oleic acid chloride was slowly added and the pH value kept constant by the addition of potassium hydroxide. After stirring for 90 minutes at 45° C., 20 ml hydrogen peroxide was added, the mass cooled to room temperature, adjusted to a pH value of 6.0 with citric acid, and homogenised.

The creamy mass was light green and had a solid substance content of 22% by weight.

EXAMPLE 4

500 g dry beans were steeped in 2000 ml water for 24 hours at room temperature and then mechanically homogenised. The pH value of the mass was adjusted to 8.0 by the addition of sodium hydroxide, stirred for 90 minutes at 50° C., and centrifuged at 10000 rev./min. The residue, which was presented in the form of 1600 g of a yellowish slightly turbid fluid with a solid substance content of 18% by weight, was mixed with 140 g palmitic acid at 50° C. while maintaining a pH value range from 7.5 to 8.0 (with the addition of sodium hydroxide).

After a reaction time of 60 minutes, 30 g monochloroacetic acid sodium salt was added, and stirring then continued for a further 30 minutes. During cooling, 20 ml hydrogen peroxide (30%) was added, and, after cooling to 25 C, a pH value of 5.5 was adjusted with citric acid.

The product consisted of a highly viscous white paste, with a solid substance content of 27% by weight.

EXAMPLE 5

The process according to Example 3 was followed, but instead of peas soya beans were used, and, instead of 144 g oleic acid chloride, 120 g palmitic acid chloride. After the reaction with the acid chloride, 1.5 g succinic acid anhydride was added while stirring, maintaining a pH value of 8.5 at 45° C. Stirring was then continued for a further 90 minutes. This mass was cooled and a pH value of 6.0 adjusted with citric acid. The product was a creamy light yellow mass with a solid substance content of 19% by weight.

EXAMPLE 6

16 g apple pectin (degree of esterisation 50%) was dissolved in 184 ml water, adjusted to a pH value of 8.0 by the addition of sodium hydroxide, and 10 g lauric acid chloride added at 55° C. while stirring. The mixture was stirred for 90 minutes while maintaining the reaction conditions. The substance was then cooled, 2 ml hydrogen peroxide (30%) added, and after 15 minutes adjusted to a pH value of 6,0 with citric acid.

The product was a light ochre-coloured creamy mass with a solid substance content of 15% by weight.

EXAMPLE 7

300 g of unsprayed citrus fruit peel was mechanically homogenised, the mass adjusted to a pH value of 8.5, and stirred for 30 minutes at 50° C. 36 g palmitic acid chloride was added, maintaining the reaction conditions, and the entire mass stirred for 60 minutes. After cooling, the pH value was adjusted to 5.5 with citric acid. The product was a light yellow creamy mass with a solid substance content of 27% by weight.

EXAMPLE 8

A green algae extract was dissolved in water, the solution adjusted with sodium hydroxide to a pH value of 8.0 to 8.5, and heated to 45° C. while stirring. Thereafter, 6–10% by weight palmitic acid chloride was added under further stirring at 45° C. and at a pH value of 8–8.5, and the mass stirred for two hours. A pH value from 5.0 to 6.5 was added with citric acid, and the mass homogenised. The product was a light yellow mass, which had a solid substance content from 20 to 50% depending on the quantity of green algae extract and the volume of palmitic acid.

EXAMPLE 9

Dry mare's milk powder was suspended in water and adjusted to a pH value of 7.5 to 8.3 with sodium hydroxide. The mixture was heated to 50° C. and cocoa fat acid chloride was added under stirring in 30 minutes. The pH value was maintained in this situation at between 7.5 and 8.5 by the addition of sodium hydroxide, and stirring was continued for a further 30 minutes. On cooling, a pH value of 5.0 to 6.0 was adjusted with malic acid or citric acid. The product was white and had a solid substance content from 4.5 to 30% by weight, depending on the volume of mare's milk and cocoa fat acid chloride used.

EXAMPLE 10

300 g whey protein was dissolved in water, the solution adjusted to a pH value of 7.0 to 8.0 with sodium carbonate solution, and heated to 45° C. under stirring. 100 g stearic acid chloride and 80 g lauric acid chloride were slowly added, and the pH value maintained at 7.0 to 8.0 by the addition of sodium carbonate solution. The mass was cooled to room temperature after two hours reaction time, and the pH value adjusted to 7,0 with citric acid. The white product had a solid substance content of 30% by weight.

EXAMPLE 11

A combination of 0.2 fractions by weight whey protein and 0.8 fractions by weight of mare's milk powder was dissolved in water, and the pH value adjusted to 7.5. This was then heated to approximately 45° C. under stirring, and 40% palmitic acid chloride related to the weight of the operational product was added to the mixture, then stirred for two hours. After cooling, the pH value was adjusted to 6.3. An almost white suspension was obtained, which became completely white after the addition of citric acid up to pH 6.0, and featured a solid content of 25% by weight.

EXAMPLE 12

The procedure was followed as in Example 11, but a combination of 0.7 fraction by weight of whey protein and 0.3 fraction by weight mare's milk powder was used. A white mass was obtained with a solid substance content of 22% by weight.

EXAMPLE 13

The procedure was followed as in Example 11, but as a biological starting material a mixture was used of 1 to 5 fractions by weight of green algae, 2 to 7 fractions by weight brown algae, and 3 to 10 fractions by weight red algae. A light brown mass was obtained with a solid substance content of 28% by weight.

EXAMPLE 14

A mixture was used of 0.5 fractions by weight whey protein and 99.5 fractions by weight dry mare's milk powder, dissolved in water, and adjusted to a pH value of 7.8 with sodium hydroxide. The mixture was heated to 45° C. under stirring. After the addition of cocoa fat acid chloride, the pH value was maintained at 7.5. After a reaction time of 2.2 hours, under stirring at 45° C., the mass was cooled. Cooling was effected very slowly. The pH was then adjusted to 6.0 with malic acid. The product was white and had a solid substance content of 24% by weight.

EXAMPLE 15

The procedure was followed as in Example 14, with the starting material being a combination of 67.6% by weight whey protein and 32.3% by weight mare's milk powder. As the fatty acid halide, a 1:1 mixture of stearic acid chloride and lauric acid chloride was used. The product obtained was a white mass with a solid substance content of 30% by weight.

EXAMPLE 16

A combination of red algae and brown algae in a proportion of 7.5:92.5 was used, and the procedure as in Example 11 was followed, with lauric acid chloride being used as the fatty acid chloride. The pH value in the base medium was adjusted to 8.5.

A pale ochre-coloured product was obtained, with a solid substance content of 35% by weight.

EXAMPLE 17

Hair shampoo and hair conditioner "2 in 1"

(designations as CTFA names)

| Phase A | |
|---|---|
| Cocamidopropyl Betaine | 10% |
| Sodium Lauryl Sulfoacetate | 25% |
| Distilled water | q.s. |
| Perfume oil | |
| Preservation agent | |
| Phase B | |
| Product as per Example 11 | 12.5% |

The manufacture of Phase A was carried out by was of water being present, and the addition, under stirring, of cocamidopropyl betaine, sodium lauryl sulfoacetate, perfume oil, and preservation agent. The mixture was then thoroughly intermixed. Phase B was then heated to 38° C., and Phase A added under stirring. This was then followed by the homo-genisation of the mixture.

EXAMPLE 18

Hair shampoo and hair conditioner "2 in 1"

The procedure as in Example 17 was followed, but the following Phase B was used:

| Phase B | |
|---|---|
| Product according to Example 1 | 2.5% |
| Product according to Example 11 | 10.0% |

EXAMPLE 19

Body cream

| Phase A | |
|---|---|
| Glyceryl Stearate/Ceteraceth-22-Ceteareth 12-ceteraryl alcohol ceryl palmitate | 3.0% |
| Cetearyl alcohol | 2.0% |
| Yoyoba oil | 1.0% |
| Phase B | |
| Distilled water | q.s. |
| Propylene glycol | 2.0% |
| Glycerine | |
| Phase C | |
| Product according to Example 9 | 1.5% |
| Product according to Example 10 | 2.0% |
| Product according to Example 14 | 2.5% |
| Preservation agent | 0.3% |
| Perfume oil | |

The manufacture of phases A and B was carried out separately under stirring at approximately 60±5° C. Both phases were then mixed with one another and homogenised. Phase C was distributed in the mixture of phases A and B at a temperature of equal to or less than 40° C., and then homogenised. A body lotion and a cosmetic mask were manufactured in the same way as in Example 19.

EXAMPLE 20

Gel

| Acrylates C10-C30-alkyl acrylate crosspolymer | 1.0% |
|---|---|
| TEA | 1.0% |
| Octyl stearate | 2.5% |
| Product from Example 8 | 5.0% |
| Preservation agent | 0.3% |
| Perfume oil (PO) as required | |
| Product from Example 16 | 2.5% |
| Distilled water | q.s. |

Manufacture took place by the gel being initially dispersed at room temperature in water and then neutralised. Oil and the products from Examples 8 and 16 were then added. The whole was well homogenised, and in conclusion mixed with PO and preservation agents.

We claim:

1. A cosmetic made of condensed plant and/or animal decomposition products comprising a product of a decomposition of a biological starting material at 20–55° C. and pH 7.5–8.5 in an aqueous solution, and subsequent condensation with a sub-stoichiometric quantity of a $C_{10}$–$C_{20}$ fatty acid halide or a $C_{10}$–$C_{20}$ fatty acid halide mixture to produce a condensation decomposition product, in which the biological starting material is selected from the group consisting of yeasts, yeast fractions, pulses, pulse fractions, pectins, pectin-containing masses, algae, algae fractions, animal milk, animal milk fractions, and their mixtures, and in which the condensation decomposition product contains biological structures of the starting material, selected from the group consisting of helical natural substance components, enzyme structures, and vitamin structures;

wherein the condensation decomposition product has a solid substance content of 4.5% to 28% by weight.

2. The cosmetic according to claim 1, wherein the biological starting material is a yeast or yeast fraction, selected from the group consisting of baker's yeast and brewer's yeast.

3. The cosmetic according to claim 1, wherein the biological starting material is a pulse or pulse fraction, selected from the group consisting of peas, lentils, soya beans and broad beans.

4. The cosmetic according to claim 1, wherein the biological starting material is a pectin or pectin-containing mass, selected from the group consisting of citrus peel, pomace, and grape daff.

5. The cosmetic according to claim 1, wherein the biological starting material is an algae, selected from the group consisting of green algae, brown algae, red algae, and their mixtures, wherein said algae comprises chlorophyll, alginates, proteins, and mineral substances.

6. The cosmetic according to claim 1, wherein the biological starting material is animal milk or a fraction thereof, selected from the group consisting of mare's milk, cow's milk, sheep's milk, reindeer milk, goat's milk, whey protein, and milk fractions.

7. The cosmetic according to claim 1, comprising a product of decomposition of a biological starting material wherein the biological starting material is subjected to mechanical shearing treatment or ultrasonic treatment prior to said condensation with a fatty acid halide.

8. The cosmetic according to claim 1, wherein the condensation product has a pH value from 5 to 7.

9. The cosmetic according to claim 1, further comprising carboxymethylization or succinylization of the condensation decomposition product.

10. The cosmetic according to claim 6, wherein the biological starting material is mare's milk.

11. The cosmetic according to claim 1, further comprising additional ancillary or carrier substances.

12. The cosmetic according to claim 11, which is selected from the group consisting of a cream, a body lotion, a hair washing agent, a hair conditioner, a mask, and a gel.

13. The cosmetic according to claim 1 wherein the condensation decomposition product is subsequently esterified or etherified.

14. The cosmetic according to claim 1,
    wherein the solid substance content ranges from 15% to 25% by weight.

15. The cosmetic according to claim 1,
    wherein the solid substance content ranges from 20% to 27% by weight.

16. A process for manufacture of a cosmetic from condensed decomposition products of plant and/or animal origin, comprising decomposing a biological starting material, selected from the group consisting of yeasts, yeast fractions, pulses, pulse fractions, pectins, pectin-containing masses, algae, algae fractions, animal milk, animal milk fractions, and their mixtures, in an alkaline medium in a pH range from 7.5 to 8.5 in a temperature range from 20 to 55° C., to produce a biological decomposition product, and condensing said biological decomposition product with a sub-stoichiometric quantity of a halide of $C_{10}$–$C_{20}$ fatty acid or a fatty acid halide of mixture of the fatty acid, to produce a condensation decomposition product, adjusting the pH value to provide an acidic medium with a pH between 5 and 7, and homogenizing without further separation, to produce a homogenate;

wherein said condensation decomposition product contains biological structures of the starting material selected from the group consisting of helical natural substance components, enzyme structures, and vitamin structures and has a solid substance content of 4.5% to 28% by weight.

17. The process according to claim 11, wherein the pH value of the alkaline medium is adjusted with an alkali metal hydroxide or alkali metal carbonate.

18. The process according to claim 11 wherein the pH value of the acidic medium is adjusted with an acid, which is selected from the group consisting of hydrochloric acid, tannic acid, malic acid, and citric acid.

19. The process according to claim 11 wherein the biological starting material decomposed by ultrasonic treatment or by mechanical shearing treatment or both, during which the temperature does not exceed 55° C. and the pH value is from 5 to 8.

20. The process according to claim 11, comprising esterifying or etherifying the biological decomposition product after condensation with the fatty acid halide.

21. The process according to claim 15, comprising carboxymethylizing the biological decomposition product with monochloroacetic acid or dichloroacetic acid, or succinylizing said product with succinic acid anhydride.

22. The process according to claim 11, comprising adding hydrogen peroxide to the biological decomposition product.

23. The process according to claim 11, further comprising mixing the homogenate with carrier or ancillary substances, and formulating into a cosmetic preparation, during which the temperature does not exceed 55° C. and the pH value of the final product is between pH 5 and 7.

24. The process according to claim 11, further comprising subjecting the biological starting material to mechanical shear treatment or ultrasonic treatment prior to said decomposing step.

25. The process according to claim 11,
   wherein the solid substance content ranges from 15% to 25% by weight.

26. The process according to claim 11,
   wherein the solid substance content ranges from 20% to 27% by weight.

* * * * *

UNITED STATES PATENT AND TRADEMARK OFFICE
CERTIFICATE OF CORRECTION

PATENT NO. : 5,916,577
DATED : June 29, 1999
INVENTOR(S) : GOLZ ET AL

It is certified that error appears in the above-indentified patent and that said Letters Patent is hereby corrected as shown below:

On the title page, column 1, after line 2 of item [87], insert --

[30]  Foreign Application Priority Data

March 23, 1995  [DE]  Germany .......... 195 10 584.2
    Feb.  05, 1996  [DE]  Germany .......... 196 05 032.4  --

Signed and Sealed this

Fifth Day of December, 2000

Attest:

Attesting Officer

Q. TODD DICKINSON

Director of Patents and Trademarks